United States Patent [19]
Parker et al.

[11] Patent Number: 5,565,068
[45] Date of Patent: Oct. 15, 1996

[54] ENERGY CONSERVATION DURING PLURAL STAGE DISTILLATION

[75] Inventors: Stuart J. Parker; Arlen G. Sliger, both of Houston; Rei-Yu J. Hwan, Sugarland, all of Tex.

[73] Assignee: Texaco Development Corporation, White Plains, N.Y.

[21] Appl. No.: 490,927

[22] Filed: Jun. 16, 1995

Related U.S. Application Data

[63] Continuation of Ser. No. 203,118, Feb. 28, 1994, abandoned.

[51] Int. Cl.$^6$ .................................................. B01D 3/00
[52] U.S. Cl. .......................... 203/25; 203/27; 203/45; 203/46; 203/78; 203/80; 203/DIG. 8; 203/DIG. 9; 568/697; 568/699; 568/913
[58] Field of Search ............... 203/DIG. 16, DIG. 8, 203/DIG. 9, DIG. 23, 18, 80, 25, 27, 78, 73, 43–46; 568/697, 699, 913

[56] References Cited

U.S. PATENT DOCUMENTS

| | | | |
|---|---|---|---|
| 4,210,495 | 7/1980 | Pinto | 203/25 |
| 4,413,150 | 11/1983 | Briggs | 203/DIG. 13 |
| 4,544,776 | 10/1985 | Osterburg et al. | 568/913 |
| 4,978,807 | 12/1990 | Smith, Jr. | 568/697 |
| 5,157,163 | 10/1992 | Smith et al. | 568/699 |
| 5,158,652 | 10/1992 | Pucci et al. | 203/80 |
| 5,250,156 | 10/1993 | Pucci et al. | 568/913 |

*Primary Examiner*—Virginia Manoharan
*Attorney, Agent, or Firm*—James L. Bailey; Kenneth R. Priem

[57] ABSTRACT

In the multistage distillation of a methyl tertiary butyl ether reaction product comprising methyl tertiary butyl ether, tertiary butyl alcohol, methanol, isobutylene and water, the methyl tertiary butyl ether reaction product is separated in a primary methyl tertiary butyl ether distillation column into a lower boiling methyl tertiary butyl ether fraction and a higher boiling aqueous tertiary butyl alcohol fraction; the lower boiling aqueous tertiary butyl alcohol fraction is separated in a tertiary butyl alcohol distillation column into a vaporized overhead tertiary butyl alcohol fraction and a higher boiling water fraction; cooling water is charged to the reflux condenser for the tertiary butyl alcohol distillation column to liquify the vaporized, overhead tertiary butyl alcohol fraction and to convert the cooling water to wet steam, and the wet steam is independently charged to the reboiler for the primary methyl tertiary butyl ether distillation zone to supply the heat necessary for the distillation to be effected therein.

7 Claims, 1 Drawing Sheet

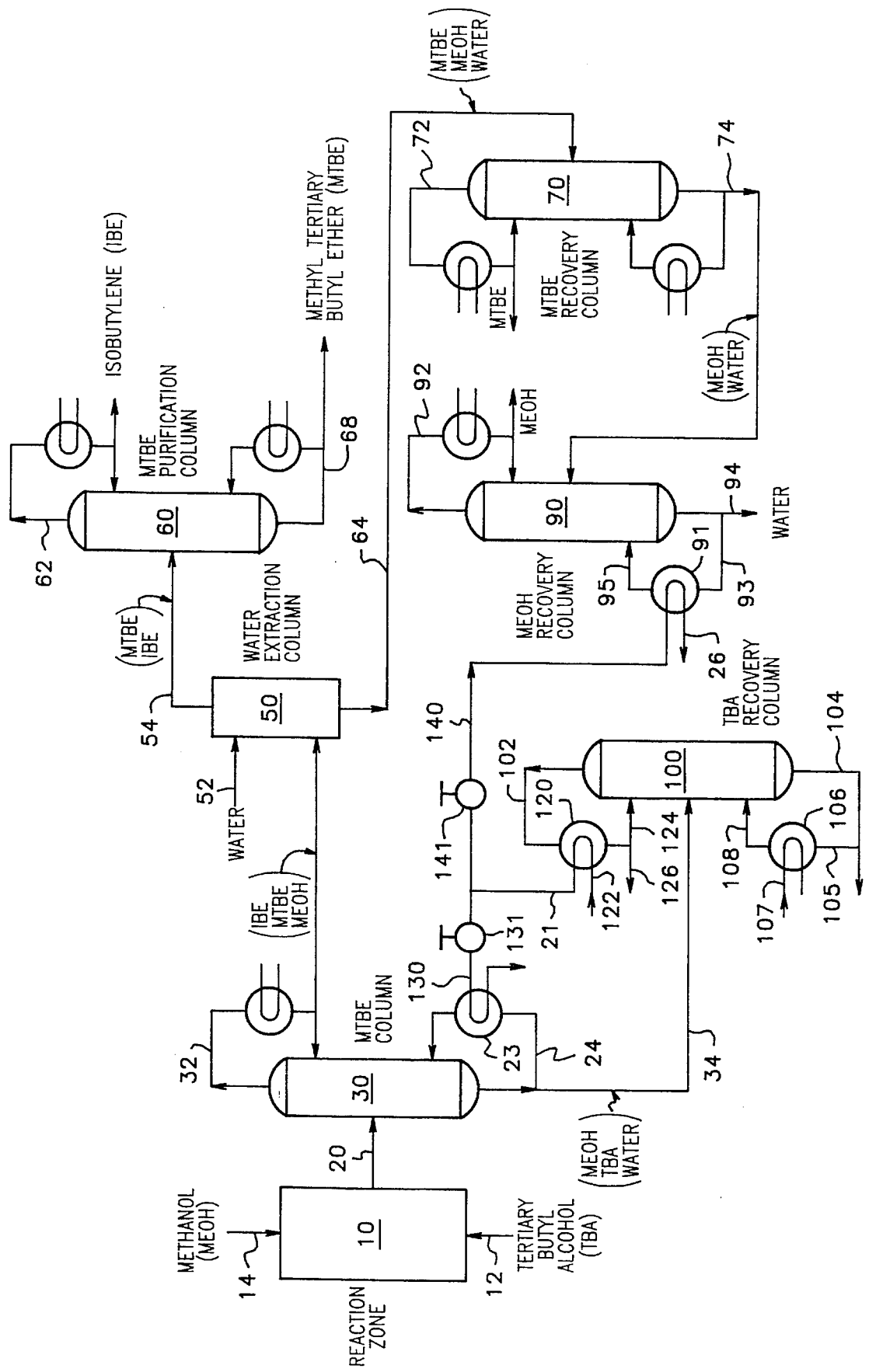

ENERGY CONSERVATION DURING PLURAL STAGE DISTILLATION

This application is a continuation of application Ser. No. 08/203,118, filed Feb. 28, 1994, now abandoned.

BACKGROUND OF THE INVENTION

1. Technical Field of the Invention

This invention relates to a multistage distillation method for the purification of a methyl tertiary butyl ether reaction product comprising methyl tertiary butyl ether, tertiary butyl alcohol, methanol, isobutylene and water wherein the methyl tertiary butyl ether reaction product is charged to a recovery zone comprising a plurality of distillation columns, each of which is equipped with a reflux condenser and a reboiler and wherein the methyl tertiary butyl ether reaction product is separated in a primary methyl tertiary butyl ether distillation column into a lower boiling methyl tertiary butyl ether distillation fraction and a higher boiling aqueous tertiary butyl alcohol fraction, wherein the higher boiling aqueous tertiary butyl alcohol fraction is separated in a tertiary butyl alcohol distillation column into a vaporized overhead tertiary butyl alcohol fraction and a higher boiling water fraction, wherein cooling water is charged to the reflux condenser for the tertiary butyl alcohol distillation column to liquify the vaporized, overhead tertiary butyl alcohol fraction and to convert the cooling water to low pressure level steam, and wherein low level steam generated in said reflux condenser for said tertiary butyl alcohol distillation column is charged to the reboiler for the primary methyl tertiary butyl ether distillation zone to supply the heat necessary for the distillation to be effected therein.

2. Prior Art

It is known to separate mixtures of organic hydrocarbons such as those present in an organic hydrocarbon reaction product by staged distillation in a distillation train comprising two or more distillation columns. Distillation columns conventionally utilize a reboiler to heat a bottoms stream to provide the thermal energy required for the distillation and a reflux condenser for condensing the vaporized overhead fraction withdrawn from the top of the distillation column. It is conventional in multistaged distillation to supply thermal energy to one distillation column by passing the hot overhead vapor or liquid distillation product from another distillation column through the reboiler heat exchanger so that the reboiler heat exchanger functions simultaneously as a reboiler for one column and as a reflux condenser for another column.

That is to say, the conventional method of heat integration is to employ condensers in one column as reboilers in another. The main drawback of the direct coupling of column exchangers is that the columns become closely coupled in duty and operation. Although minor changes in temperature and reflux rates can be accommodated by adjustment of the reflux condenser, significant changes in the operation of one of the columns inevitably upsets the other in return. For example, start-up and shut-down operations become complicated and tricky because all of the associated equipment must be manipulated simultaneously. Also, to avoid control interactions due to changes in liquid level, the reboilers columns generally must be elevated above the receiver of the heat supplier column. This contributes significantly to construction costs and maintenance costs.

It is known to generate steam in a cumene distillation column for use as a heating medium for a reboiler of a phenol distillation column.

SUMMARY OF THE INVENTION

The process of the present invention is useful in the manufacture of methyl tertiary butyl ether. The reaction product formed during a methyl tertiary butyl ether manufacturing process may comprise isobutylene, methyl tertiary butyl ether, methanol, tertiary butyl alcohol and water. A plural stage distillation train is used comprising a plurality of distillation columns, each distillation column being equipped with a reflux condenser and a reboiler; the distillation train including a primary methyl tertiary butyl ether distillation column, a water extraction column, a methyl tertiary butyl ether purification column, a methyl tertiary butyl ether recovery column, a methanol recovery column, and a tertiary butyl alcohol distillation column. The methyl tertiary butyl ether reaction product is separated in the primary methyl tertiary butyl ether distillation column into an isobutylene and methanol-containing lower boiling methyl tertiary butyl ether distillation fraction and a lower boiling aqueous tertiary butyl alcohol fraction. The higher boiling aqueous tertiary butyl alcohol fraction is separated in the tertiary butyl alcohol distillation column into a vaporized overhead tertiary butyl alcohol distillation fraction and a higher boiling water fraction. Also, the isobutylene and methanol-containing higher boiling methyl tertiary butyl ether distillation fraction is separated in a water extraction zone into an isobutylene-containing methyl tertiary butyl ether extract and a raffinate comprising methyl tertiary butyl ether, methanol and water.

The isobutylene-containing methyl tertiary butyl ether extract is separated in the methyl tertiary butyl ether purification column into a lower boiling isobutylene fraction and a lower boiling purified methyl tertiary butyl ether product fraction. The raffinate is separated in a methyl tertiary butyl ether recovery column into a lower boiling methyl tertiary butyl ether fraction and a lower boiling aqueous methanol fraction. The aqueous methanol fraction, in turn, is separated in the methanol recovery column into a lower boiling methanol fraction and a higher boiling water fraction.

In accordance with the present invention, cooling water is charged to the reflux condenser for the tertiary butyl alcohol distillation column to liquify the vaporized methyl tertiary butyl alcohol distillation fraction whereby the cooling water is converted to low pressure (i.e., low level) steam. The low pressure steam generated in the reflux condenser for the tertiary butyl alcohol distillation column is charged to the reboiler for the primary methyl tertiary butyl ether distillation column to supply the heat necessary for the distillation to be effected therein.

In accordance with a modification of the present invention, a portion of the low pressure steam generated in the reflux condenser for the tertiary butyl alcohol distillation column is charged in parallel to the reboiler for the methanol recovery column to supply the heat necessary for the distillation to be effected therein.

BRIEF DESCRIPTION OF THE DRAWING

The drawing is a schematic flow sheet with conventional parts omitted showing the general recovery sequence of the present invention.

DESCRIPTION OF THE PREFERRED EMBODIMENT

Turning now to the drawing, there is shown a schematic flow sheet illustrating the preferred method for the practice of the present invention. In the drawing, conventional parts such as valves, pumps, temperature controllers, sensors, pressure sensors, flow control regulation apparatus, heaters, coolers, etc., have been omitted and the reflux condensers and the reboilers have been schematically illustrated.

In accordance with the present invention, there is provided an etherification reaction zone 10 containing a bed of a solid etherification catalyst. Any suitable etherification catalyst may be used, for example, a solid resin etherification catalyst such as a strongly acidic ion exchange resin consisting essentially of sulfonated polystyrene crosslinked with divinyl benzene (e.g., Dowex 50, Nalcite HCR, Amberlyst 15, etc.). As another example, the catalyst may be a fluorophosphoric acid-on-titania catalyst of the type disclosed in Knifton et al. U.S. Pat. No. 4,822,921 or a heteropoly acid such as 12-tungsto-phosphoric acid or 12-molybdophosphoric acid supported on an inert support such as titania.

Tertiary butyl alcohol is charged to the reaction zone 10 by a tertiary butyl alcohol feed line 12 and methanol is charged by a methanol charge line 14. The flow of methanol and tertiary butyl alcohol to the reaction zone 10 is regulated so that a molar excess of methanol is present in the line 14 leading to the etherification reaction zone 10, such as, for example, a molar ratio of about 1.1 to about 2 moles of methanol per mol of tertiary butyl alcohol.

Within the etherification reaction zone 10, the feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

Within the etherification reaction zone 10, methanol will exothermicly react with the tertiary butyl alcohol to form methyl tertiary butyl ether which will be contained in a reaction product discharged from the etherification reaction zone 10 by way of a line 20 leading to a primary methyl tertiary butyl ether (MTBE) distillation column 30.

As a specific example, when the solid etherification catalyst is a sulfonic acid resin such as Amberlyst 15 and when the molar ratio of methanol to tertiary butyl alcohol in the feed mixture charged to the etherification reaction zone 10 has a ratio of about 2 moles of methanol per mole of tertiary butyl alcohol, and the reaction is conducted at a temperature of about 100° C. at a feed rate of about 2 volumes of feed mixture per volume of catalyst per hour, the etherification reaction product may have the composition in part shown by the following table:

| ETHERIFICATION REACTION PRODUCT | |
|---|---|
| Component | % |
| Water | 14.0 |
| Methanol | 27.6 |
| Isobutylene | 3.0 |
| TBA[1] | 14.1 |
| MTBE[2] | 34.5 |
| Other[3] | 6.8 |

[1]Tertiary butyl alcohol.
[2]Methyl tertiary butyl ether.
[3]Includes the acetone, propanol, ditertiary butyl peroxide, tertiary butyl formate, etc. initially present in the tertiary butyl alcohol feedstock.

The etherification reaction product charged to the primary MTBE distillation column 30 by way the charge line 20 is fractionated therein under distillation conditions including a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia, the distillation conditions being selected such that substantially all of the MTBE in the etherification reaction product 20 is taken overhead from the first distillation column 30 by a line 32. As a consequence, the first distillation fraction 32 taken overhead from the distillation column 30 will comprise substantially all of the isobutylene and substantially all of the methyl tertiary butyl ether and some of the methanol charged to the first distillation column 30. A higher boiling heavier distillation fraction 34 discharged from the first MTBE distillation column 30 will comprise methanol, tertiary butyl alcohol and water.

In accordance with the present invention, the lower boiling methyl tertiary butyl ether distillation fraction 32 is charged to an aqueous solvent extraction zone 50 where it is countercurrently contacted with water introduced into the solvent extraction zone 50 by a charge line 52.

Within the aqueous solvent extraction zone 50, solvent extraction conditions are established for countercurrent solvent extraction including a ratio of higher boiling methyl tertiary butyl ether distillation feed fraction 32 to water within the range of about 0.8 to about 1.8 volumes of feed per volume of water per hour, and more preferably a ratio of about 1.0 to about 1.5 volumes of feed fraction 32 per volume of water. Extraction conditions may suitably include a temperature of about 20° to about 60° C., and more preferably from about 30° to about 40° C., and a pressure of about 50 to about 500 psia, and more preferably from about 50 to about 150 psia.

As a consequence, a supernatant extract will be formed which is withdrawn from the methanol solvent extraction zone 50 by line 54 leading to MTBE purification column 60. The raffinate is discharged from the solvent extraction zone 50 by way of a bottoms charge line 64 leading to a methyl tertiary butyl ether recovery distillation zone 70.

Within the methyl tertiary butyl ether purification distillation zone 60, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a lower boiling aqueous isobutylene distillation fraction 62 discharged from the distillation zone 60 and a higher boiling product distillation fraction 68 consisting essentially of methyl tertiary butyl ether.

The raffinate 64 charged to the methyl tertiary butyl ether recovery column 70 will comprise methyl tertiary butyl ether, methanol and water, and is suitably fractionated therein under distillation conditions including a liquid reflux temperature of about 30° to about 90° C., and more preferably from about 50° to about 75° C., and a reboiler temperature of about 80° to about 120° C., and more preferably from about 105° to about 115° C., and a pressure of about 15 to about 60 psia, and more preferably from about 40 to about 50 psia, to form a lower boiling methyl tertiary butyl ether distillation fraction 72 comprising methyl tertiary butyl ether which may suitably be recycled by a recycle line (not shown) to the methanol solvent extraction zone 50. A higher boiling aqueous methanol distillation fraction comprising water and methanol is discharged from the third distillation zone 70 by a line 74 leading to a methanol recovery column 90. The aqueous methanol distillation fraction charged to the methanol recovery column 90 is fractionated therein under distillation conditions which may suitably include a liquid reflux temperature of about 30° to about 80° C., and more preferably from about 60° to about 75° C., a reboiler temperature of about 100° to about 140° C., and more preferably from about 110° to about 120° C., and a pressure of about 15 to about 60 psia, and more preferably from about 20 to about 30 psia, into a lower boiling methanol distillation fraction 92 and a higher boiling water fraction 94 which may be discharged from the system.

The aqueous methanol-containing tertiary butyl alcohol fraction 34 discharged from the primary methyl tertiary butyl ether distillation column 30 is charged to a tertiary butyl alcohol recovery distillation column 100 where it is fractionated under distillation conditions including a liquid reflux temperature of about 35° to about 170° C., and more preferably about 140° to about 150° C., and a reboiler temperature of about 100° to about 190° C., more preferably about 170° to about 180° C. and at a pressure of about 15 to about 190 psia, and more preferably about 110 to about 160 psia, into a lower boiling distillation fraction comprising tertiary butyl alcohol and methanol discharged by a line 102 and a higher boiling water fraction 104 that may be discharged from the system.

The lighter tertiary butyl alcohol distillation fraction 102 may be recycled to the etherification reaction zone 10 by an appropriate recycle line (not shown).

In accordance with the present invention, the heat required for the distillation to be effected in the tertiary butyl alcohol recovery column 100 is provided by charging high pressure steam through a line 107 to a heat exchanger 106 where it is used to heat a portion of the water from line 104, which is passed through the heat exchanger 106 by a line 105. The water in line 105 is heated, for example, to a temperature of about 170° to about 180° C. at a pressure of about 110 to about 160 psia and then returned to the tertiary butyl ether recovery column 100 by line 108.

The vaporized tertiary butyl alcohol fraction is taken overhead by line 102 from the distillation column 100 at a temperature, for example of about 145° to about 155° C. It is charged to a heat exchanger 120 and cooled therein and liquified to a temperature of about 140° to about 150° C. by cooling water, such as boiler feed water, charged to the heat exchanger 120 by a water feed line 122. A desired portion of the liquified tertiary butyl alcohol is returned to the tertiary butyl ether recovery column 100 by a reflux line 124 and the remainder is recovered by a line 126 for recycle or storage.

The boiler feed water charged to the heat exchanger 120 by the water feed line 122 is converted to low pressure, wet steam in the heat exchanger 120 by the hot vaporized tertiary butyl alcohol overhead 102 and is withdrawn by a line 21.

In accordance with the present invention, the low pressure steam in the line 21 is charged by a line 130 controlled by a valve 131 to a heat exchanger, or reboiler 23, for the methyl tertiary butyl ether distillation column 30 to provide the heat required for the distillation to be effected therein. In accordance with this embodiment, a portion of the aqueous methanol-containing tertiary butyl alcohol fraction 34 is routed by a branch line 24 to the reboiler 23 where it is heated by the low pressure steam charged by line 21, for example, to a temperature of about 90° to 110° C. at a pressure of about 15 to 65 psia.

In accordance with one embodiment of the present invention, the low pressure steam in the line 21 will be routed by a line 140 controlled by a valve 141 to a reboiler 91 for the methanol recovery column 90 where it will be used to heat the bottoms water fraction discharged from the column 90 by the line 94. In accordance with this embodiment, a portion of the water in the line 94 is routed by a line 93 to the reboiler where it will be heated to temperature of about 110° to about 120° C. at a pressure of about 20 to 30 psia by the low pressure steam charged to the reboiler 91 by the line 140. The heated water will be returned to the methanol recovery column 90 by a line 95 and spent steam will be discharged from the reboiler 91 by a spent steam discharge line 26.

SPECIFIC EXAMPLE

By way of specific example, the reaction product charged to the primary distillation column 30 by the line 20 may comprise about 2 wt. % methanol, about 14.5 wt. % tertiary butyl alcohol, about 14 wt. % water, about 3 wt. % isobutylene and about 34.5 wt. % of methyl tertiary butyl ether.

This reaction product is separated in the distillation column 30 into a higher boiling methyl tertiary butyl ether distillation fraction 32 comprising about 6.5 wt. % isobutylene, about 16.5 wt. % methanol, about 75 wt. % methyl tertiary butyl ether and a lower boiling aqueous tertiary butyl alcohol fraction 34 comprising about 37 wt. % methanol, about 26 wt. % tertiary butyl alcohol and about 26 wt. % of water.

In accordance with the preferred embodiment of the present invention, the liquid reflux temperature in the first reflux condenser 15 for the column 30 suitably will be about 40° to about 80° C. and the reboiler temperature in the reboiler 23 suitably will be from about 95° to about 105° C. The first distillation column 30 will be operated at a pressure of about 15 to about 60 psia, the distillation conditions being selected such that substantially all of the methyl tertiary butyl ether charged to the distillation column 30 is taken overhead with the first overhead distillation product 32.

The tertiary butyl alcohol recovery distillation column 100 suitably will be operated at a liquid reflux temperature of about 140° to about 150° C. and at a reboiler temperature of about 170° to about 180° C. The distillation column 100 will be operated at a pressure of about 110 to about 160 psia.

High pressure steam is charged to the reboiler 106 for the tertiary butyl alcohol recovery column 100 which is operated at a reboiler temperature of about 170° to about 180° C. at a pressure of about 110 to about 160 psia. Heat is supplied to the reboiler 106 by a high pressure steam. The overhead vaporized tertiary butyl alcohol fraction 102 withdrawn from the column 100 by the line 102 is liquified in reflux condenser 120 at a temperature of about 140° to about 150° C. at a pressure of about 110 to 160 psia with boiler feed water charged to the heat exchanger by water feed line 122.

The boiler feed water is converted to low pressure steam in the heat exchanger 120 and is discharged therefrom by steam line 21 leading by way of line 130 to the reboiler 23 for the primary methyl tertiary butyl ether distillation column 30 where it is used to heat an aqueous tertiary butyl alcohol stream charged by line 11 to a temperature of about 95° to about 105° C. at a pressure of about 15 to 60 psia. The heated aqueous tertiary butyl alcohol stream is returned to the methyl tertiary butyl ether distillation column 30 by a return line 13.

Having thus described our invention, what is claimed is:

1. In a multistage distillation method for the purification of a methyl tertiary butyl ether reaction product comprising methyl tertiary butyl ether, tertiary butyl alcohol, methanol, isobutylene and water, the improvement which comprises the steps of:

charging said methyl tertiary butyl ether reaction product to a recovery zone comprising a plurality of distillation columns equipped with reflux condensers and reboilers and including a primary methyl tertiary butyl ether distillation column operated at a reboiler temperature of about 80° to about 115° C. and a reboiler pressure of about 15 to 60 psia and a tertiary butyl alcohol distillation column operated at an overhead temperature of about 140° C. to about 160° C. and a reboiler pressure of about 110 to 160 psia, separating said methyl tertiary butyl ether reaction product in said primary methyl tertiary butyl ether distillation column into a lower boiling methyl tertiary butyl ether, isobutylene and methanol-containing distillation fraction and a higher boiling aqueous tertiary butyl alcohol fraction and separating said higher boiling aqueous tertiary butyl alcohol fraction in said tertiary butyl alcohol distillation column into a vaporized overhead tertiary butyl alcohol distillation fraction and a higher boiling water fraction, charging cooling water to the reflux condenser for said tertiary butyl alcohol distillation column to liquify the vaporized overhead tertiary butyl alcohol distillation fraction whereby the cooling water is converted to low pressure steam, and charging low pressure steam generated in said reflux condenser for said tertiary butyl alcohol distillation column to the reboiler for said primary methyl tertiary butyl ether distillation column to supply the heat necessary for the distillation to be effected therein.

2. A method as in claim 1 wherein the primary methyl tertiary butyl ether distillation column is operated at a reflux temperature of about 30° to about 100° C., a reboiler temperature of about 90° to about 110° C. and a reboiler pressure of about 15 to 65 psia.

3. A method as in claim 2 wherein the primary methyl tertiary butyl ether distillation column is operated at a reboiler temperature of about 95° to about 105° C.

4. A method as in claim 1 wherein the tertiary butyl alcohol distillation column is operated at an overhead vapor temperature of about 145° to about 155° C., and a reboiler temperature of about 170° to about 180° C.

5. In a multistage distillation method for the purification of a methyl tertiary butyl ether reaction product comprising methyl tertiary butyl ether, tertiary butyl alcohol, methanol, isobutylene and water, the improvement which comprises the steps of:

charging said methyl tertiary butyl ether reaction product to a recovery zone comprising a plurality of distillation columns equipped with reflux condensers and reboilers and including a primary methyl tertiary butyl ether distillation column, a water extraction column, a methyl tertiary butyl ether purification column, a methyl tertiary butyl ether recovery column, a methanol recovery column, and a tertiary butyl alcohol distillation column, separating said methyl tertiary butyl ether reaction product in said primary methyl tertiary butyl ether distillation column into a lower boiling methyl tertiary butyl ether, isobutylene and methanol-containing distillation fraction and a higher boiling aqueous tertiary butyl alcohol fraction, separating said higher boiling aqueous tertiary butyl alcohol fraction in said tertiary butyl alcohol distillation column into a vaporized overhead tertiary butyl alcohol distillation fraction and a higher boiling water fraction, separating said lower boiling methyl tertiary butyl ether, isobutylene and methanol-containing distillation fraction in a water extraction zone into an isobutylene-containing methyl tertiary butyl ether extract and a raffinate comprising methyl tertiary butyl ether alcohol, methanol and water, separating said isobutylene-containing methyl tertiary butyl ether extract in said methyl tertiary butyl ether purification column into a lower boiling water-containing isobutylene fraction and a higher boiling purified methyl tertiary butyl ether fraction, separating said raffinate in a methyl tertiary butyl ether recovery column into a lower boiling methyl tertiary butyl ether fraction and a higher boiling aqueous methanol fraction, separating said aqueous methanol fraction in said methanol recovery column into a lower boiling methanol fraction and a higher boiling water fraction, charging cooling water to the reflux condenser for said tertiary butyl alcohol distillation column to liquify the vaporized overhead tertiary butyl alcohol distillation fraction whereby the cooling water is converted to low pressure steam, charging a portion of the low pressure steam generated in said reflux condenser for said tertiary butyl alcohol distillation column to the reboiler for said primary methyl tertiary butyl ether distillation column to supply the heat necessary for the distillation to be effected therein, and charging another portion of the low pressure steam generated in said reflux condenser for said tertiary butyl alcohol distillation column to the reboiler for said methanol recovery column to supply the heat necessary for the distillation to be effected therein.

6. A method as in claim 5 wherein the primary methyl tertiary butyl distillation column is operated at a reflux temperature of about 30° to about 100° C., a reboiler temperature of about 90° to about 115° C. and a reboiler pressure of about 15 to 65 psia., wherein the tertiary butyl alcohol distillation column is operated at an overhead vapor temperature of about 140° to about 160° C., and a reboiler temperature of about 100° to about 190° C. and a reboiler pressure of about 15 to 190 psia, wherein the methyl tertiary butyl ether purification column is operated at a reflux temperature of about 30° to about 60° C. a reboiler temperature of about 100° to about 140° C., a reboiler pressure of about 70 to 120 psia, wherein the methyl tertiary butyl ether recovery column is operated at a reflux temperature of about 30° to about 90° C., a reboiler temperature of about 80° to about 120° C., a reboiler pressure of about 15 to 60 psia, and wherein the methanol recovery column is operated at a reflux temperature of about 30° to about 80° C., a reboiler temperature of about 100° to about 140° C. and a reboiler pressure of about 15 to 65 psia.

7. A method as in claim 5 wherein the primary methyl tertiary butyl distillation column is operated at a reflux temperature of about 40° to about 80° C., a reboiler temperature of about 90° to about 105° C. and a reboiler pressure of about 15 to 65 psia., wherein the tertiary butyl alcohol distillation column is operated at an overhead vapor temperature of about 145° to about 155° C., and a reboiler temperature of about 170° to about 180° C. and a reboiler pressure of about 110 to 160 psia, wherein the methyl tertiary butyl ether purification column is operated at a reflux temperature of about 40° to about 55° C., a reboiler temperature of about 125° to about 135° C., a reboiler pressure of about 90 to 110 psia, wherein the methyl tertiary butyl ether recovery column is operated at a reflux temperature of about 50° to about 75° C., a reboiler temperature of about 105° to about 115° C., a reboiler pressure of about 40 to 50 psia, and wherein the methanol recovery column is operated at a reflux temperature of about 60° to about 75° C., a reboiler temperature of about 110° to about 120° C. and a reboiler pressure of about 20 to 30 psia.

\* \* \* \* \*